(12) United States Patent
Brady et al.

(10) Patent No.: US 10,004,596 B2
(45) Date of Patent: Jun. 26, 2018

(54) ACCOMMODATING INTRAOCULAR LENS DEVICE

(71) Applicant: LensGen, Inc., Irvine, CA (US)

(72) Inventors: Daniel Brady, San Juan Capistrano, CA (US); Thomas Silvestrini, Alamo, CA (US); Ramgopal Rao, Irvine, CA (US)

(73) Assignee: LensGen, Inc., Irvine, CA (US)

( * ) Notice: Subject to any disclaimer, the term of this patent is extended or adjusted under 35 U.S.C. 154(b) by 0 days. days.

(21) Appl. No.: 14/447,621

(22) Filed: Jul. 31, 2014

(65) Prior Publication Data

US 2016/0030161 A1 Feb. 4, 2016

(51) Int. Cl.
*A61F 2/16* (2006.01)

(52) U.S. Cl.
CPC .......... *A61F 2/1635* (2013.01); *A61F 2/1629* (2013.01); *A61F 2/1648* (2013.01); *A61F 2002/1697* (2013.01)

(58) Field of Classification Search
None
See application file for complete search history.

(56) References Cited

U.S. PATENT DOCUMENTS

| | | |
|---|---|---|
| 4,373,218 A | 2/1983 | Schachar |
| 4,512,040 A | 4/1985 | McClure |
| 4,585,457 A | 4/1986 | Kalb |
| 4,720,286 A | 1/1988 | Bailey et al. |
| 4,731,078 A | 3/1988 | Stoy et al. |
| 4,822,360 A | 4/1989 | Deacon |
| 4,842,601 A | 6/1989 | Smith |
| 4,888,012 A | 12/1989 | Horn et al. |
| 4,892,543 A * | 1/1990 | Turley ............... A61F 2/1613 623/6.13 |

(Continued)

FOREIGN PATENT DOCUMENTS

| | | |
|---|---|---|
| EP | 0766540 B1 | 8/1999 |
| WO | WO 2004/054471 | 7/2004 |

(Continued)

OTHER PUBLICATIONS

Extended European Search Report and Opinion dated Jan. 20, 2017 for EP Application No. 14857916.2. (9 pages).

(Continued)

*Primary Examiner* — Leslie Lopez
(74) *Attorney, Agent, or Firm* — Shepppard Mullin Richter & Hampton LLP

(57) ABSTRACT

An accommodating intraocular lens (IOL) can be implanted either alone or as part of a two-part lens assembly. The IOL comprises an optic, a flexible membrane and a peripheral edge coupling the optic and the flexible membrane. The peripheral edge comprises an external circumferential surface having a height and a force transmitting area defined along a portion of the height of the external circumferential surface. A closed volume spaces apart the optic and the flexible membrane. The optic is axially displaced and the flexible membrane changes in curvature about a central axis when a radial compressive force is applied to the force transmitting area. A volume defined by the closed volume remains fixed when the optic is axially displaced and the flexible membrane changes in curvature and/or when the radial compressive force is applied to the force transmitting area.

8 Claims, 6 Drawing Sheets

(56) References Cited

U.S. PATENT DOCUMENTS

| | | |
|---|---|---|
| 4,932,966 A | 7/1990 | Christie et al. |
| 5,035,710 A | 7/1991 | Nakada et al. |
| 5,074,876 A | 12/1991 | Kelman |
| 5,091,121 A | 2/1992 | Nakada et al. |
| 5,152,788 A | 10/1992 | Isaacson et al. |
| 5,275,623 A | 1/1994 | Sarfarazi |
| 5,443,506 A | 8/1995 | Garabet |
| 5,489,302 A | 2/1996 | Skottun |
| 5,607,472 A | 3/1997 | Thompson |
| 6,117,171 A | 9/2000 | Skottun |
| 6,197,057 B1 | 3/2001 | Peyman et al. |
| 6,730,123 B1 | 5/2004 | Klopotek |
| 6,855,164 B2 | 2/2005 | Glazier |
| 6,930,838 B2 | 8/2005 | Schachar |
| 7,063,723 B2 | 6/2006 | Ran |
| 7,122,053 B2 | 10/2006 | Esch |
| 7,217,288 B2 | 5/2007 | Esch et al. |
| 7,220,279 B2 | 5/2007 | Nun |
| 7,229,475 B2 | 6/2007 | Glazier |
| 7,247,168 B2 | 7/2007 | Esch et al. |
| 7,261,737 B2 | 8/2007 | Esch et al. |
| 7,416,562 B2 | 8/2008 | Gross |
| 7,438,723 B2 | 10/2008 | Esch |
| 7,453,646 B2 | 11/2008 | Lo |
| 7,485,144 B2 | 2/2009 | Esch |
| 7,637,947 B2 | 12/2009 | Smith et al. |
| 7,675,686 B2 | 3/2010 | Lo et al. |
| 7,753,953 B1 | 7/2010 | Yee |
| 7,776,088 B2 | 8/2010 | Shadduck |
| 7,815,678 B2 | 10/2010 | Nun |
| 7,842,087 B2 | 11/2010 | Nun |
| 7,854,764 B2 | 12/2010 | Nun |
| 7,857,850 B2 | 12/2010 | Mentak et al. |
| 7,981,155 B2 | 7/2011 | Cumming |
| 7,985,253 B2 | 7/2011 | Cumming |
| 7,998,199 B2 | 8/2011 | Nun |
| 8,018,658 B2 | 9/2011 | Lo |
| 8,034,106 B2 | 10/2011 | Mentak et al. |
| 8,034,107 B2 | 10/2011 | Stenger |
| 8,038,711 B2 | 10/2011 | Clarke |
| 8,048,155 B2 | 11/2011 | Shadduck |
| 8,052,752 B2 | 11/2011 | Woods et al. |
| 8,070,806 B2 | 12/2011 | Khoury |
| 8,158,712 B2 | 4/2012 | Your |
| 8,197,541 B2 | 6/2012 | Schedler |
| 8,216,306 B2 | 7/2012 | Coroneo |
| 8,254,034 B1 | 8/2012 | Shields et al. |
| 8,273,123 B2 | 9/2012 | Nun |
| 8,314,927 B2 | 11/2012 | Choi et al. |
| 8,320,049 B2 | 11/2012 | Huang et al. |
| 8,328,869 B2 | 12/2012 | Smiley et al. |
| 8,361,145 B2 | 1/2013 | Scholl et al. |
| 8,398,709 B2 | 3/2013 | Nun |
| 8,414,646 B2 | 4/2013 | De Juan, Jr. et al. |
| 8,425,599 B2 | 4/2013 | Shadduck |
| 8,447,086 B2 | 5/2013 | Hildebrand et al. |
| 8,454,688 B2 | 6/2013 | Esch et al. |
| 8,475,529 B2 | 7/2013 | Clarke |
| 8,545,556 B2 | 10/2013 | Woods et al. |
| 8,585,758 B2 | 11/2013 | Woods |
| 8,608,800 B2 | 12/2013 | Portney |
| 8,657,878 B2 | 2/2014 | Mentak et al. |
| 8,715,345 B2 | 5/2014 | DeBoer et al. |
| 8,715,346 B2 | 5/2014 | De Juan, Jr. et al. |
| 8,734,509 B2 | 5/2014 | Mentak et al. |
| 8,771,347 B2 | 7/2014 | DeBoer et al. |
| 8,814,934 B2 | 8/2014 | Geraghty et al. |
| 8,834,565 B2 | 9/2014 | Nun |
| 8,867,141 B2 | 10/2014 | Pugh et al. |
| 8,900,298 B2 | 12/2014 | Anvar et al. |
| 2003/0093149 A1 | 5/2003 | Glazier |
| 2003/0105522 A1 | 6/2003 | Glazier |
| 2003/0109926 A1 | 6/2003 | Portney |
| 2003/0149480 A1 | 8/2003 | Shadduck |
| 2004/0082993 A1 | 4/2004 | Woods |
| 2004/0082994 A1 | 4/2004 | Woods et al. |
| 2004/0111153 A1 | 6/2004 | Woods et al. |
| 2004/0148023 A1* | 7/2004 | Shu ............... A61F 2/1613 623/6.34 |
| 2004/0162612 A1 | 8/2004 | Portney et al. |
| 2004/0169816 A1 | 9/2004 | Esch |
| 2004/0181279 A1 | 9/2004 | Nun |
| 2005/0071002 A1 | 3/2005 | Glazier |
| 2005/0107873 A1 | 5/2005 | Zhou |
| 2005/0119740 A1 | 6/2005 | Esch et al. |
| 2005/0137703 A1 | 6/2005 | Chen |
| 2005/0149183 A1* | 7/2005 | Shadduck ............. A61F 2/1613 623/6.13 |
| 2005/0251253 A1 | 11/2005 | Gross |
| 2005/0251254 A1 | 11/2005 | Brady et al. |
| 2006/0041307 A1 | 2/2006 | Esch et al. |
| 2006/0047339 A1 | 3/2006 | Brown |
| 2006/0074487 A1 | 4/2006 | Gilg |
| 2006/0100701 A1 | 5/2006 | Esch et al. |
| 2006/0155372 A1 | 7/2006 | Coroneo |
| 2006/0212116 A1 | 9/2006 | Woods |
| 2007/0010880 A1 | 1/2007 | Esch |
| 2007/0021831 A1 | 1/2007 | Clarke |
| 2007/0032868 A1 | 2/2007 | Woods |
| 2007/0050024 A1 | 3/2007 | Zhang |
| 2007/0078515 A1 | 4/2007 | Brady et al. |
| 2007/0088433 A1 | 4/2007 | Esch et al. |
| 2007/0100445 A1 | 5/2007 | Shadduck |
| 2007/0106377 A1* | 5/2007 | Smith ............... A61F 2/1613 623/6.13 |
| 2007/0118216 A1 | 5/2007 | Pynson |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0185574 A1 | 8/2007 | Nun |
| 2007/0203578 A1 | 8/2007 | Scholl et al. |
| 2007/0213817 A1 | 9/2007 | Esch et al. |
| 2007/0244561 A1 | 10/2007 | Nun |
| 2007/0260210 A1 | 11/2007 | Richardson |
| 2007/0260310 A1 | 11/2007 | Richardson |
| 2008/0004699 A1 | 1/2008 | Nun |
| 2008/0015689 A1 | 1/2008 | Esch et al. |
| 2008/0033547 A1 | 2/2008 | Chang et al. |
| 2008/0046074 A1 | 2/2008 | Smith et al. |
| 2008/0046075 A1 | 2/2008 | Esch et al. |
| 2008/0154364 A1 | 6/2008 | Richardson et al. |
| 2008/0188930 A1 | 8/2008 | Mentak et al. |
| 2008/0269887 A1 | 10/2008 | Cumming |
| 2008/0300680 A1 | 12/2008 | Nun |
| 2008/0306588 A1 | 12/2008 | Smiley et al. |
| 2008/0306589 A1 | 12/2008 | Donitzky et al. |
| 2009/0005865 A1 | 1/2009 | Smiley et al. |
| 2009/0027661 A1 | 1/2009 | Choi et al. |
| 2009/0149952 A1 | 6/2009 | Shadduck |
| 2009/0204210 A1 | 8/2009 | Pynson |
| 2009/0264998 A1 | 10/2009 | Mentak et al. |
| 2009/0292355 A1* | 11/2009 | Boyd ............... A61F 2/1635 623/6.34 |
| 2009/0319040 A1 | 12/2009 | Khoury |
| 2010/0030332 A1 | 2/2010 | Schedler |
| 2010/0094412 A1 | 4/2010 | Wensrich |
| 2010/0121444 A1 | 5/2010 | Nun |
| 2010/0131058 A1 | 5/2010 | Shadduck |
| 2010/0179653 A1* | 7/2010 | Argento ............. A61F 2/1635 623/6.13 |
| 2010/0211169 A1 | 8/2010 | Stanley et al. |
| 2010/0228344 A1 | 9/2010 | Shadduck |
| 2010/0288346 A1 | 9/2010 | Esch |
| 2010/0324672 A1 | 12/2010 | Esch et al. |
| 2010/0324674 A1 | 12/2010 | Brown |
| 2011/0029074 A1 | 2/2011 | Reisin et al. |
| 2011/0082544 A1 | 4/2011 | Nun |
| 2011/0112636 A1 | 5/2011 | Nun |
| 2011/0118834 A1 | 5/2011 | Lo et al. |
| 2011/0118836 A1 | 5/2011 | Jain |
| 2011/0160852 A1 | 6/2011 | Mentak et al. |
| 2011/0224788 A1 | 9/2011 | Webb |
| 2011/0282442 A1 | 11/2011 | Scholl et al. |

(56) References Cited

U.S. PATENT DOCUMENTS

| | | |
|---|---|---|
| 2011/0288638 A1 | 11/2011 | Smiley et al. |
| 2012/0035724 A1 | 2/2012 | Clarke |
| 2012/0071972 A1 | 3/2012 | Zhao |
| 2012/0078361 A1 | 3/2012 | Shadduck |
| 2012/0078364 A1 | 3/2012 | Stenger |
| 2012/0150292 A1 | 6/2012 | Mentak et al. |
| 2012/0253459 A1 | 10/2012 | Reich et al. |
| 2012/0290084 A1 | 11/2012 | Coroneo |
| 2012/0296423 A1 | 11/2012 | Caffey et al. |
| 2012/0296424 A1 | 11/2012 | Betser |
| 2012/0303118 A1 | 11/2012 | DeBoer et al. |
| 2012/0310341 A1 | 12/2012 | Simonov et al. |
| 2012/0310343 A1 | 12/2012 | Van Noy |
| 2013/0006353 A1 | 1/2013 | Betser et al. |
| 2013/0018461 A1 | 1/2013 | Nun |
| 2013/0035760 A1 | 2/2013 | Portney |
| 2013/0038944 A1 | 2/2013 | Chang et al. |
| 2013/0110234 A1 | 5/2013 | DeVita et al. |
| 2013/0110235 A1 | 5/2013 | Shweigerling |
| 2013/0116781 A1 | 5/2013 | Nun |
| 2013/0131794 A1 | 5/2013 | Smiley et al. |
| 2013/0190867 A1 | 7/2013 | Peyman |
| 2013/0226295 A1 | 8/2013 | De Juan, Jr. et al. |
| 2013/0231741 A1 | 9/2013 | Clarke |
| 2013/0250239 A1 | 9/2013 | Hildebrand et al. |
| 2013/0268070 A1 | 10/2013 | Esch et al. |
| 2013/0297018 A1 | 11/2013 | Brady et al. |
| 2013/0317607 A1 | 11/2013 | DeBoer et al. |
| 2014/0012277 A1 | 1/2014 | Matthews et al. |
| 2014/0058507 A1 | 2/2014 | Reich et al. |
| 2014/0085726 A1 | 3/2014 | Portney |
| 2014/0100654 A1 | 4/2014 | Portney et al. |
| 2014/0107459 A1 | 4/2014 | Lind et al. |
| 2014/0111765 A1 | 4/2014 | DeBoer et al. |
| 2014/0121768 A1 | 5/2014 | Simpson |
| 2014/0135917 A1 | 5/2014 | Glazier |
| 2014/0135918 A1 | 5/2014 | De Juan, Jr. et al. |
| 2014/0172092 A1 | 6/2014 | Carson et al. |
| 2014/0180404 A1 | 6/2014 | Tran |
| 2014/0180405 A1 | 6/2014 | Weinschenk, III et al. |
| 2014/0180406 A1 | 6/2014 | Simpson |
| 2014/0180410 A1 | 6/2014 | Gerardi |
| 2014/0227437 A1 | 8/2014 | DeBoer et al. |
| 2014/0228949 A1 | 8/2014 | Argento et al. |
| 2014/0249625 A1 | 9/2014 | Shadduck |
| 2014/0257478 A1 | 9/2014 | McCafferty |
| 2014/0257479 A1 | 9/2014 | McCafferty |
| 2015/0216652 A1 | 8/2015 | Jansen |
| 2016/0317286 A1 | 11/2016 | Brady et al. |
| 2016/0317287 A1 | 11/2016 | Silvestrini et al. |

FOREIGN PATENT DOCUMENTS

| | | | |
|---|---|---|---|
| WO | WO2009015226 A3 | 1/2009 | |
| WO | WO 2010/010565 A2 * | 1/2010 | ............. A61F 2/16 |
| WO | WO2011/137191 A1 | 11/2011 | |
| WO | WO2013016804 A1 | 2/2013 | |
| WO | WO 2013/166068 | 11/2013 | |
| WO | WO2014152017 A1 | 9/2014 | |

OTHER PUBLICATIONS

International Search Report and Written Opinion dated Apr. 20, 2017 for PCT/US2016/064491. (14 pages).

International Search Report and Written Opinion dated Feb. 11, 2015 for PCT/US2014/063538. (6 pages).

International Search Report and Written Opinion dated Oct. 26, 2015 for PCT/US2015/042513. (10 pages).

* cited by examiner

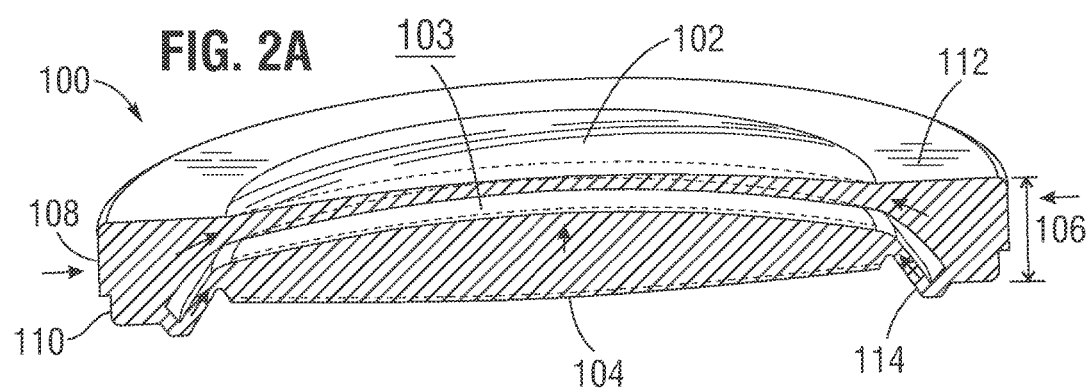
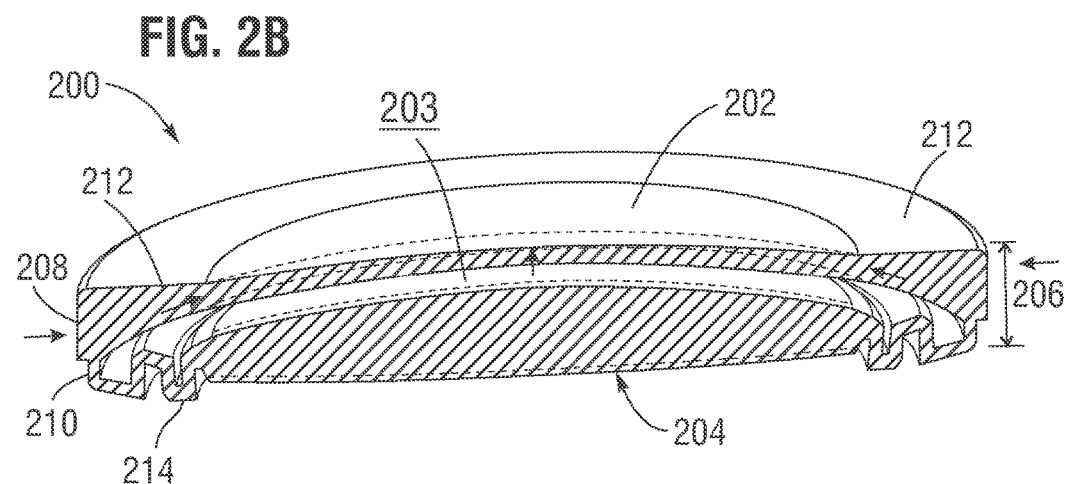

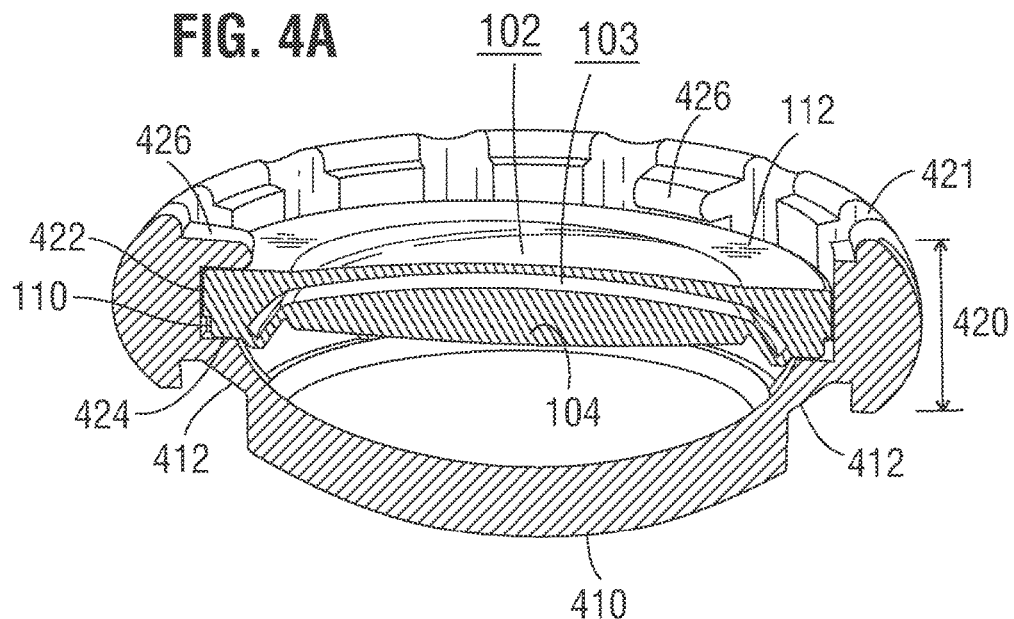
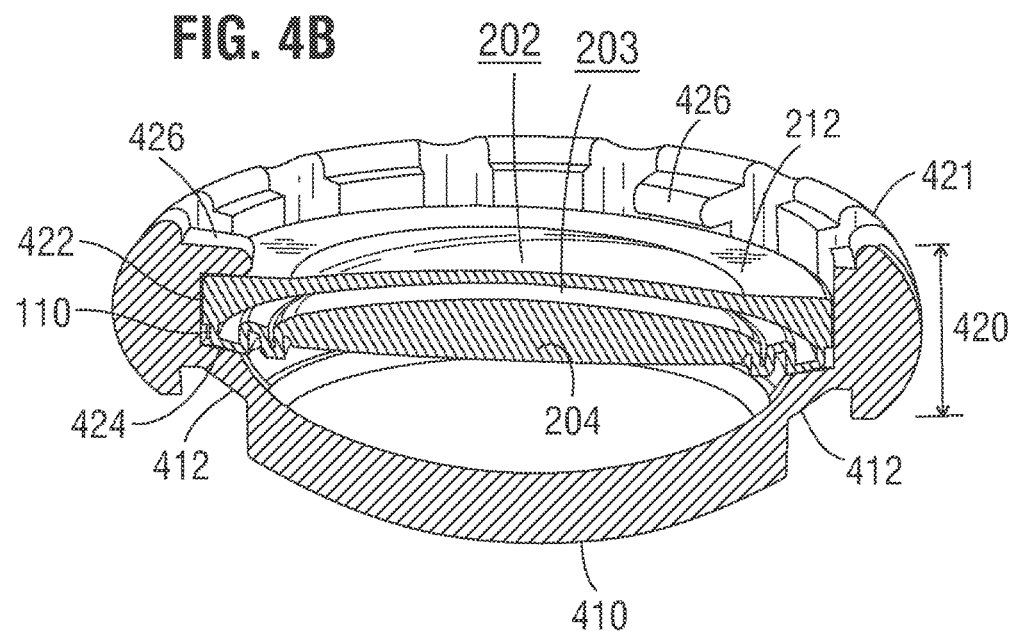

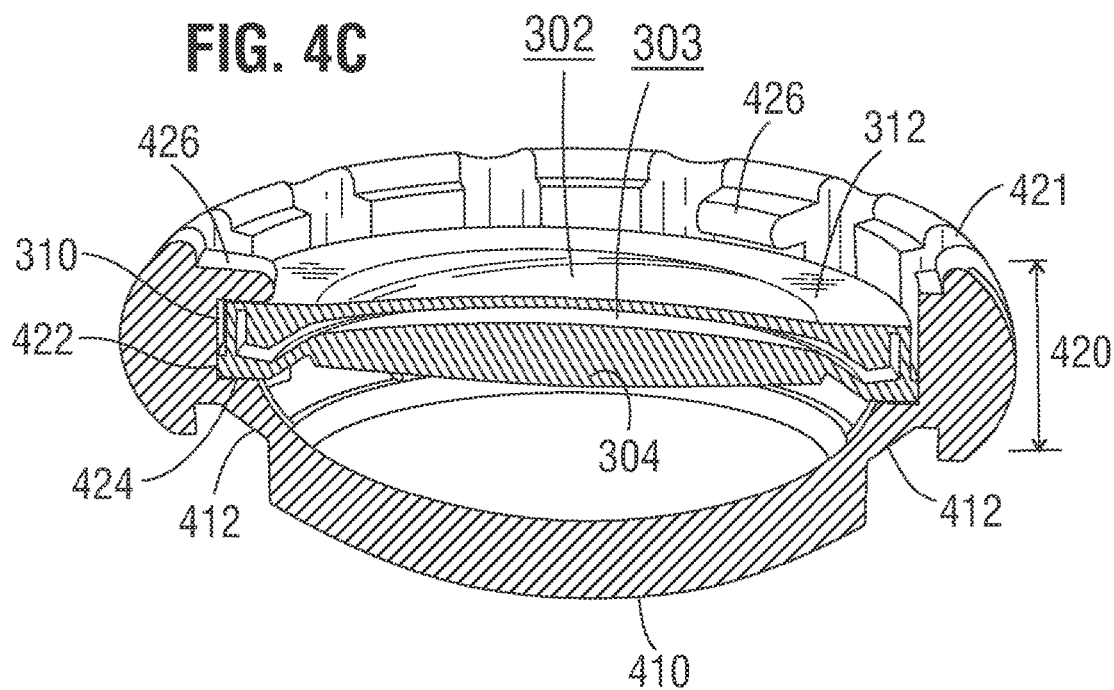

ACCOMMODATING INTRAOCULAR LENS DEVICE

FIELD OF THE INVENTION

The invention relates generally to an accommodating intraocular lens device and, more particularly, to an accommodating intraocular lens device configured for implantation in a lens capsule or suclus of a subject's eye.

BACKGROUND

Surgical procedures on the eye have been on the rise as technological advances permit for sophisticated interventions to address a wide variety of ophthalmic conditions. Patient acceptance has increased over the last twenty years as such procedures have proven to be generally safe and to produce results that significantly improve patient quality of life.

Cataract surgery remains one of the most common surgical procedures, with over 16 million cataract procedures being performed worldwide. It is expected that this number will continue to increase as average life expectancies continue to rise. Cataracts are typically treated by removing the crystalline lens from the eye and implanting an intraocular lens ("IOL") in its place. As conventional IOL devices are primarily focused for distance visions, they fail to correct for presbyopia and reading glasses are still required. Thus, while patients who undergo a standard IOL implantation no longer experience clouding from cataracts, they are unable to accommodate, or change focus from near to far, from far to near, and to distances in between.

Surgeries to correct refractive errors of the eye have also become extremely common, of which LASIK enjoys substantial popularity with over 700,000 procedures being performed per year. Given the high prevalence of refractive errors and the relative safety and effectiveness of this procedure, more and more people are expected to turn to LASIK or other surgical procedures over conventional eyeglasses or contact lens. Despite the success of LASIK in treating myopia, there remains an unmet need for an effective surgical intervention to correct for presbyopia, which cannot be treated by conventional LASIK procedures.

As nearly every cataract patient also suffers from presbyopia, there is convergence of market demands for the treatment of both these conditions. While there is a general acceptance among physicians and patients of having implantable intraocular lens in the treatment of cataracts, similar procedures to correct for presbyopia represent only 5% of the U.S. cataract market. There is therefore a need to address both ophthalmic cataracts and/or presbyopia in the growing aging population.

BRIEF SUMMARY

The accommodating intraocular lens (IOL) described herein combine the power changing feature of a flexible membrane with a base lens. The power changing feature of the IOL is driven by fluid optics within a closed volume. One significant advantage of the IOL is that the closed volume that spaces apart the flexible membrane and the base lens maintains a substantially constant volume and avoids many of the problems associated with fluid optic IOLs which involve or require a changing volume, i.e., fluid being fed into the chamber from reservoirs. The many disadvantages exhibited by fluid optics requiring changing volumes include non-uniform power change and/or non-uniform buckling of the flexible membrane. The IOLs disclosed herein avoid such problems by maintaining a substantially constant or fixed volume and maintaining good optical quality throughout the range of power change. The fluid redistributes itself within a closed volume as the power changes. This design requires a significantly smaller volume of fluid than known IOL fluid optics that require a reservoir. An additional benefit of this invention by virtue of being a smaller IOL, is a reduction of biocompatibility issues associated with larger IOLs as well as reducing the incision size required to implant the lens. This results in faster healing and a more stable refraction.

The IOLs disclosed herein may be configured in any number of ways. In one embodiment, the radially compressive forces exerted on an implanted IOL may be concentrated onto the flexible membrane to cause the flexible membrane to change in curvature. At the same time, the IOL is configured such that the radially compressive forces are minimized or reduced with respect to the optic. The optic, however, may be configured to axially displace toward the flexible membrane in response to its change in curvature. This axial displacement may be facilitated by coupling the optic to the peripheral edge of the IOL in a manner that permits the optic to float. As the flexible membrane changes in curvature, fluid adhesion or surface tension will operate to pull the optic toward the flexible membrane. Preferably, the optic resists or does not change in curvature.

In another embodiment, the radially compressive forces exerted on the implanted IOL may be concentrated onto the optic to cause the optic to axially displace. In a preferred embodiment, the optic resists or does not itself change in curvature. At the same time, the IOL is configured such that the radially compressive forces are minimized or reduced with respect to the flexible membrane. The flexible membrane, however, will change in curvature in response to the axial displacement of the lens.

In a further embodiment, the radially compressive forces exerted on the implanted IOL may be applied to both the flexible membrane and the optic to cause the change in curvature of the flexible membrane and the axial displacement of the optic toward the flexible membrane, while at the same time maintaining a constant volume of the space therebetween. Preferably, the flexible membrane changes in curvature while the optic is axially displaced and resists or does not change in curvature.

With respect to any of the embodiments, the thickness of the membrane may be uniform or it may be varied. In one embodiment, the membrane may have a thinner central region and a thicker peripheral region, about the central axis A-A, which may permit a larger power change for a given amount of force. However, if the ratio of thicknesses of the central to the peripheral regions of the membrane is too large, significant asphericity may result, reducing the optical quality under compression and making it more difficult to manufacture. A thicker membrane in the center may make it easier to manufacture the IOL but may reduce the potential power change. The determination of the optimal membrane thickness and uniformity of thickness is determined to maximize power change and optical quality while minimizing manufacturing issues and cost. The membrane must also be thick enough to permit handling during the implantation procedure.

The two-part accommodating IOL devices disclosed herein provides for a number of advantages owing to its separate two-part construction. Implantation of the IOL device requires a significantly reduced incision size, as the two parts of the IOL device are implanted separately and thus significantly reducing the delivery profile for implantation. The reduced incision size provides for a number of advantages, including obviating the need for anesthesia and sutures to close the incision site and improved surgical outcomes.

Additionally, greater control is afforded with respect to adjusting the sizing and the power of the IOL during surgery. Implanting the base lens assembly into the lens capsule will provide the physician an impression as to the size of the patient's lens capsule and will thus help verify the correct size of the power changing lens that will subsequently be implanted.

In one embodiment, an accommodating IOL is described. The IOL comprises an optic, a flexible membrane and a peripheral edge coupled to the optic and the flexible membrane. The peripheral edge comprises an external circumferential surface having a height and a force transmitting area defined along a portion of the height of the external circumferential surface. A closed volume spaces apart the optic and the flexible membrane. Preferably, the optic is axially displaced and the flexible membrane changes in curvature about a central axis when a radial compressive force is applied to the force transmitting area. The optic has greater rigidity than the membrane such that the optic resists bending or changing in curvature when the optic is axially displaced and/or when the radial compressive force is applied to the force transmitting area. Alternatively the IOL can be implanted into the sulcus. The IOL can be designed so that it could be implanted into the sulcus of an eye with or without the natural crystalline lens (phakic or pseudophakic IOL).

In accordance with a first aspect, the force transmitting area is a circumferential ring. Preferably, the circumferential ring protrudes outwardly from the circumferential peripheral edge.

In accordance with a second aspect, a fluid is contained within the closed volume. Preferably, the fluid is selected from the group consisting of: silicone oil, fluorinated silicone oil and polyphenyl ether.

In accordance with a third aspect, the accommodating IOL further comprises a haptic is in contact with or coupled to the force transmitting area.

In accordance with a fourth aspect, the closed volume is defined between the optic, the flexible membrane and the peripheral edge.

In accordance with a fifth aspect, a volume defined by the closed volume remains fixed when the optic is axially displaced and the flexible membrane changes in curvature and/or when the radial compressive force is applied to the force transmitting area.

In another embodiment, a two-piece accommodating intraocular lens assembly is described. The two-piece accommodating intraocular lens assembly comprises a base lens assembly and the accommodating IOL described herein. The base assembly comprises a base power optic and a haptic system circumferentially around the base power optic. The haptic system comprises an internal surface facing the base power optic and defining an internal space within which the accommodating IOL is removably maintained.

In accordance with a first aspect, only the force transmitting area of the external circumferential surface is in contact with the internal surface of the haptic system.

In accordance with a second aspect, the base lens assembly further comprises supporting flanges extending radially inwardly from the internal surface to contact a side of the IOL that comprises the optic and/or the flexible membrane.

In accordance with a third aspect, a plurality of spaced notches is disposed around an external surface of the haptic system.

In accordance with a fourth aspect, the base power optic may either partially or completely resist changes in curvature or may change in curvature in response to a radially compressive force applied to the haptic system.

In a further embodiment, an accommodating IOL is described. The accommodating IOL comprises an optic, a flexible membrane, and a circumferential peripheral edge comprising internal and external sides. A closed volume spaces apart the optic and the flexible membrane. An optic coupler and a membrane coupler are disposed from the internal side of the circumferential peripheral edge. A force transmitting area is disposed on the external side of the circumferential peripheral edge. The force transmitting area is located along a portion of the external side that opposes the optic coupler and is not located along a portion of the external side that opposes the membrane coupler. The force transmitting area concentrates the transmission of a radially compressive force applied thereon to the optic via the optic coupler to cause axial displacement of the optic along a central axis. Axial displacement of the optic causes a change in curvature of the flexible membrane as a result of the closed volume and adhesion of the fluid to the membrane.

In accordance with a first aspect, the force transmitting area is a circumferential ring. Preferably, the circumferential ring protrudes outwardly from the circumferential peripheral edge.

In accordance with a second aspect, a fluid is contained within the closed volume. Preferably, the fluid is selected from the group consisting of: silicone oil, fluorinated silicone oil and polyphenyl ether.

In accordance with a third aspect, the optic has greater rigidity than the membrane such that the optic resists bending or changing in curvature when the optic is axially displaced and/or when the radial compressive force is applied to the force transmitting area.

In accordance with a fourth aspect, a circumferential channel is defined between the internal side of the circumferential peripheral edge and the flexible membrane, the circumferential channel having an internal volume that is included within the closed volume.

In accordance with a fifth aspect, a haptic is in direct contact with or coupled to the force transmitting area.

In accordance with a sixth aspect, the closed volume is defined between the optic, the flexible membrane and the circumferential peripheral edge.

In accordance with a seventh aspect, the volume of the closed volume remains fixed when the radially compressive force is applied to the force transmitting area.

In yet a further embodiment, a two-piece accommodating intraocular lens assembly is described. The two-piece accommodating intraocular lens assembly comprises a base lens assembly and the accommodating IOL described here. The base assembly comprises a base power optic and a haptic system circumferentially around the base power optic, the haptic system having an internal surface defining an internal space within which the accommodating IOL is removably maintained.

In accordance with a first aspect, only the force transmitting area of the external side is in contact with the internal surface of the haptic system.

In accordance with a second aspect, the base lens assembly further comprises supporting flanges extending radially inwardly from the internal surface to contact a side of the IOL that comprises the optic and/or the flexible membrane.

In accordance with a third aspect, a plurality of spaced notches is disposed around an external surface of the haptic system.

In accordance with a fourth aspect, the base power optic may either partially or completely resist changes in curvature or may change in curvature in response to a radially compressive force applied to the haptic system.

In another embodiment, an accommodating IOL comprises an optic, a flexible membrane and a circumferential peripheral edge comprising internal and external sides. A closed volume provides a space between the optic and the flexible membrane. An optic coupler and a membrane coupler are each disposed from the internal side of the circumferential peripheral edge. A force transmitting area is disposed on the external side of the circumferential peripheral edge, the force transmitting area being located along a portion of the external side that opposes the membrane coupler and not being located along a portion of the external side that opposes the optic coupler. The force transmitting area concentrates the transmission of a radially compressive force applied thereon to the flexible membrane via the membrane coupler to cause a change in curvature of the flexible membrane about a central axis. A change in curvature of the flexible membrane causes a corresponding axial displacement of the optic as a result of the closed volume and adhesion of the fluid to the optic.

In accordance with a first aspect, the force transmitting area is a circumferential ring. Preferably, the circumferential ring protrudes outwardly from the circumferential peripheral edge.

In accordance with a second aspect, a fluid is contained within the closed volume. Preferably, the fluid is selected from the group consisting of: silicone oil, fluorinated silicone oil and polyphenyl ether.

In accordance with a third aspect, the optic coupler comprises a plurality of folded areas to permit the optic to freely displace axially along a central axis in response to the changes in curvature of the flexible membrane and/or when the radially compressive force is applied to the force transmitting area.

In accordance with a fourth aspect, a haptic is in direct contact with or coupled to the force transmitting area.

In accordance with a fifth aspect, the closed volume is defined between the optic, the flexible membrane and the circumferential peripheral edge.

In accordance with a sixth aspect, the closed volume remains fixed when the radially compressive force is applied to the force transmitting area.

In yet another embodiment, a two-piece accommodating intraocular lens assembly is described. The two-piece accommodating intraocular lens assembly comprises a base lens assembly and the accommodating IOL described herein. The base assembly comprises a base power optic and a haptic system circumferentially around the base power optic. The haptic system defines an internal space within which the accommodating IOL is removably maintained.

In accordance with a first aspect, only the force transmitting area of the external side is in contact with an internal surface of the haptic system.

In accordance with a second aspect, the base lens assembly further comprises supporting flanges extending radially inwardly from the internal surface to contact a side of the IOL that comprises the optic and/or the flexible membrane.

In accordance with a third aspect, a plurality of spaced notches disposed around an external surface of the haptic system.

In accordance with a fourth aspect, the base power optic may either partially or completely resist changes in curvature or may change in curvature in response to a radially compressive force applied to the haptic system.

In yet a further embodiment, an accommodating IOL is provided. The IOL comprises an optic, a flexible membrane and a force transmitting area coupled to the optic and the flexible membrane. A closed volume spaces apart the optic and the flexible membrane. The optic is axially displaced and the flexible membrane changes in curvature about a central axis when a radial compressive force is applied to the force transmitting area. The optic has greater rigidity than the membrane such that the optic resists bending or changing in curvature when the optic is axially displaced and/or when the radial compressive force is applied to the force transmitting area.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which:

FIGS. 2A-2B are cross-sectional views of alternate embodiments of the accommodating IOL taken along 2AB-2AB of FIG. 1A.

FIG. 4A is a cross-sectional view of the two-piece accommodating intraocular lens assembly comprising the accommodating IOL of FIG. 2A assembled within the base lens assembly of FIG. 3A.

FIG. 4B is a cross-sectional view of the two-piece accommodating intraocular lens assembly comprising the accommodating IOL of FIG. 2B assembled within the base lens assembly of FIG. 3A.

FIG. 4C is a cross-sectional view of the two-piece accommodating intraocular lens assembly comprising the accommodating IOL of FIG. 2C assembled within the base lens assembly of FIG. 3A.

Like numerals refer to like parts throughout the several views of the drawings.

DETAILED DESCRIPTION OF THE PREFERRED EMBODIMENTS

Specific, non-limiting embodiments of the present invention will now be described with reference to the drawings. It should be understood that such embodiments are by way of example and are merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

The contents of the following commonly-owned and co-pending U.S. patent applications are incorporated herein by reference as if fully set forth herein: U.S. patent application Ser. No. 13/662,087, filed Oct. 26, 2012, published as U.S. Pub. No. 2013/0053954 on Feb. 28, 2013; U.S. patent application Ser. No. 13/725,895, filed Dec. 21, 2012, published as U.S. Pub. No. 2014/0180403 on Jun. 26, 2014; U.S. Patent Appl. Ser. No. 61/899,110, filed Nov. 1, 2013 and U.S. Patent Appl. Ser. No. 61/899,106, filed Nov. 1, 2013.

Figure 1A:
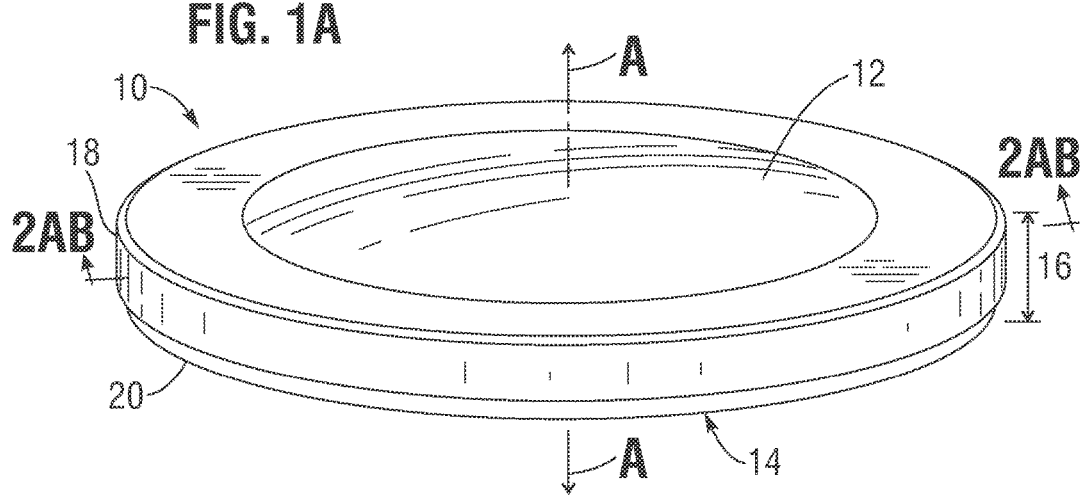
FIGS. 1A-1B are perspective views of alternate embodiments of the accommodating IOL.

FIG. 1A depicts an embodiment of an accommodating IOL 10, comprising a flexible membrane 12, an optic 14 and a peripheral edge 16 coupling the flexible membrane 12 and the optic 14. The peripheral edge 16 is depicted as having a height and a circumference. A portion of the height adjacent the flexible membrane 12 is stepped outwardly to define a force transmitting area 18 and a portion of the height adjacent the optic 14 is stepped inwardly 20 to define an area that minimizes contact with or maintains a gap or a spaced relation to either a lens capsule or sulcus of an eye into which it is implanted or a base assembly, as depicted in FIGS. 4A and 4B. In a preferred embodiment, the central axis A-A of the accommodating IOL 10 preferably coincides about the optical axis of the eye, which traverses the center of the eye's cornea (not depicted) through the retina. The accommodating IOL 10 of FIG. 1A can be configured in any number of alternate embodiments, including the embodiments depicted in FIGS. 2A and 2B.

Figure 1B:
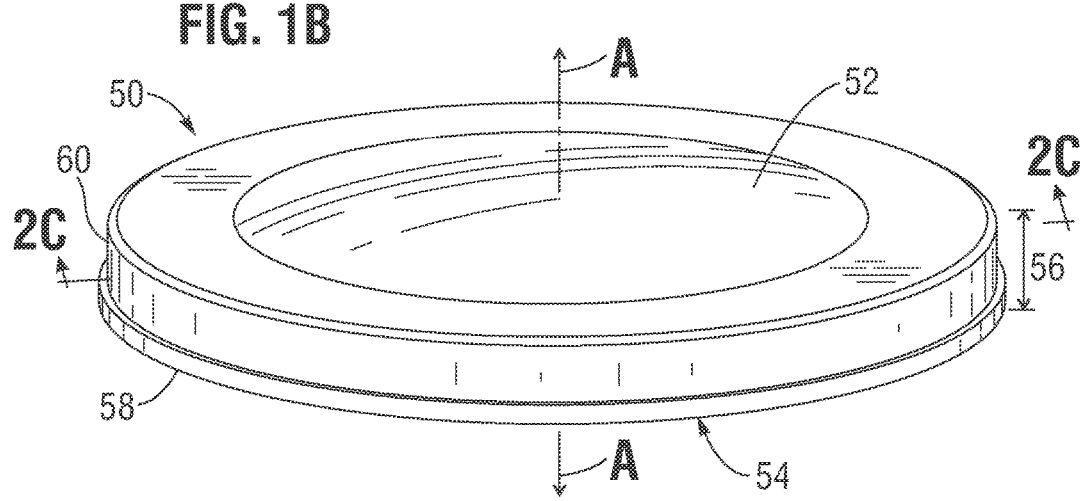

FIG. 1B depicts another embodiment of the accommodating IOL 50, comprising a flexible membrane 52, an optic 54 and a peripheral edge 56 coupling the flexible membrane 52 and the optic 54. As with the accommodating IOL 10 of FIG. 1A, the peripheral edge 56 is depicted as having a height and a circumference. In the accommodating IOL 50 of FIG. 1B, however, the portion of the height that is stepped outwardly to define a force transmitting area 58 is adjacent the optic 54 and the portion that is stepped inwardly 60 to define an area that minimizes contact with or maintains a gap or a spaced relation to either the lens capsule or sulcus when implanted or a base assembly, as depicted in FIG. 4C, is adjacent the flexible membrane 52. As with the embodiment of the accommodating IOL 10 of FIG. 1A, the central axis A-A of the accommodating IOL 50 preferably coincides about the optical axis of the eye. The accommodating IOL 50 of FIG. 1B can be configured in any number of embodiments, including the embodiment depicted in FIG. 2C.

As illustrated in FIGS. 1A and 1B, the force transmitting areas 18, 58 are located at a different location relative to the peripheral edge 16, 56. The different locations of the force transmitting areas 18, 58 function to concentrate the transmission of radially compressive forces applied to the IOLs 10, 50 when implanted in a capsular bag or sulcus of an eye during accommodation. The mechanism of accommodation of a natural eye and the implantation of an accommodating IOL is described more fully in U.S. Ser. Nos. 61/889,106 and 61/899,110, the entire contents of which are incorporated by reference as if fully set forth herein. Once implanted in the lens capsule or sulcus of the eye, the IOL 10, 50 experiences radially compressive forces resulting from the relaxation of the ciliary muscles during accommodation. The force transmitting areas 18, 58 are in direct contact with the capsular bag or suclus and therefore capture or concentrate the transmission of the radially compressive forces onto the IOL and, in particular, to the specific IOL structure which is connected or adjacent to the force transmitting area 18, 58.

The force transmitting area 18 in the IOL 10 in FIG. 1A is located on the opposing side of the flexible membrane 12. By virtue of this location, the force transmitting area 18 concentrates and transmits the radially compressive forces onto the flexible membrane 12 to cause a deformation or change in curvature of the flexible membrane 12. The force transmitting area 18 in this embodiment preferably does not extend to the side opposing the optic 14 so as to limit or prevent the transmission of the radially compressive forces onto the optic 14. In contrast, the stepped in portion 20 experiences little, if any, of the radially compressive forces by providing a gap or a spaced relation to the capsular bag or sulcus of the eye into which it is implanted or the base assembly, depicted as 110 and 210 in FIGS. 4A and 4B, respectively.

The force transmitting area 58 in the IOL 50 of FIG. 1B is located on the opposing side of the optic 54. By virtue of this location, the force transmitting area 58 concentrates and transmits the radially compressive forces onto the optic 54 to cause an axial displacement of the optic 54 along A-A. The direction of the axial displacement will depend on the manner in which the optic 54 is coupled to the peripheral edge 56, i.e., either vaulted toward or away from the flexible membrane 52. In the embodiments depicted in FIG. 2C, the optic 304 is vaulted toward the flexible membrane 302 and thus will respond to the radially compressive forces by axial displacement toward the flexible membrane 302. Again, in contrast, the stepped in portion 310 experiences little, if any, of the radially compressive forces by providing a gap or a spaced relation to the capsular bag or sulcus of the eye into which it is implanted or the base assembly, as depicted in FIG. 4C. Preferably, the optic 54 resists any changes in curvature during axial displacement or when the radially compressive forces act upon the force transmitting area 58.

Figure 2C:
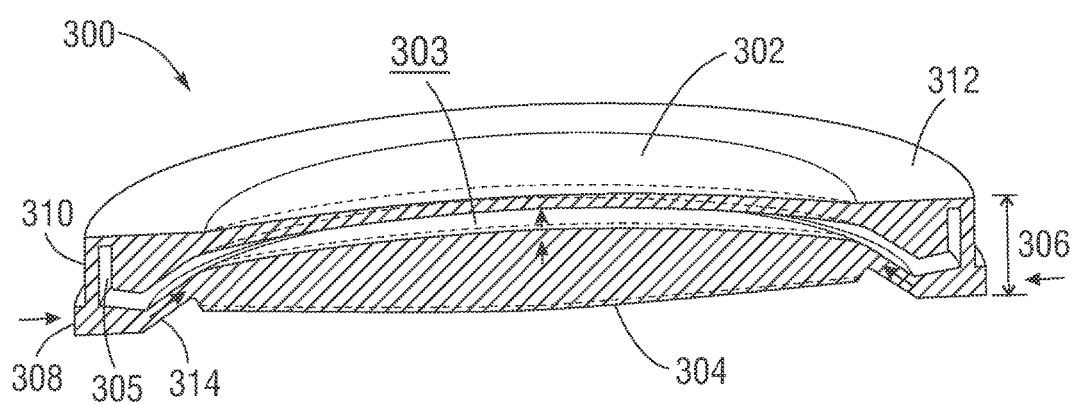
FIG. 2C is a cross-sectional view of another embodiment of the accommodating IOL taken along 2C-2C of FIG. 1B.

FIGS. 2A-2C depict various alternative embodiments of the IOL based on either the IOL 10 of FIG. 1A or the IOL 50 of FIG. 1B.

FIG. 2A depicts an IOL 100 comprising a flexible membrane 102, an optic 104 and a circumferential peripheral edge 106 coupling the flexible membrane 102 and the optic 104. A membrane coupler 112 is disposed from the internal side of the circumferential peripheral edge 106 to couple the membrane 102 with the peripheral edge 106. Similarly, an optic coupler 114 is disposed from the internal side of the circumferential peripheral edge 106 to couple the optic 104 to with the peripheral edge 106. Preferably, the optic coupler 114 is angled toward the flexible membrane 102 such that it vaults the optic 104 toward the flexible membrane 102.

The circumferential peripheral edge 106 comprises at least two areas. A force transmitting area 108 and a stepped-in area 110. The force transmitting area 108 is intended to contact and engage the lens capsule or sulcus of an eye when implanted directly into the lens capsule or sulcus or contact the internal surface 422 of the base lens assembly 400 when used as part of a two-piece accommodating intraocular lens assembly (see FIG. 4A). The force transmitting area 108 concentrates the transmission of a radially compressive force applied thereon to the flexible membrane 102 via the membrane coupler 112 to cause a change of curvature of the flexible membrane 102. Thus, the force transmitting area 108 is disposed on the external side of the circumferential peripheral edge 106 and located along a portion of the external side that opposes the membrane coupler 112 and preferably is not located along a portion of the external side that opposes the optic coupler 114. The portion of the side that opposes the optic coupler 114 is preferably the stepped-in area 110.

A closed volume 103 is provided within the IOL 100 to space apart the flexible membrane 102 and the optic 104. The closed volume 103 is not in fluid communication externally of the IOL 100 and therefore its volume remains fixed. As a result of the fixed volume and the vaulting of the optic 104 toward the flexible membrane 102 by the optic coupler 114, the flexible membrane 102 and the optic 104 do not diverge away from one another substantially when radially compressive forces are applied to the force transmitting area 108. The extension of the closed volume 103 beyond the circumference of the optic 104 functions to further isolate the optic 104 from directly experiencing the radially compressive forces exerted on the force transmitting area 108.

The change in curvature of the flexible membrane 102 provides the accommodative power change, with radially compressive force. As the flexible membrane 102 changes in curvature, the optic 104 axially displaces toward the flexible membrane 102. This permits the flexible membrane 102 to change shape in an optically uniform manner with a constant volume of fluid, thereby avoiding the problems of non-uniform buckling of the flexible membrane. The dotted lines in FIG. 2A depict the change in curvature of the flexible membrane 102 and the axial displacement of the optic 104 in the presence of an radially compressive force upon the force transmitting area 108 to produce the desired diopter change. As FIG. 2A shows the deformation of the membrane at the dotted line is smooth and would have good optical quality. High period buckling is eliminated which avoids creating a wavy or rippled surface that would have poor optical quality.

FIG. 2B depicts an alternate embodiment of an IOL 200. As with the IOL 100 in FIG. 2A, the IOL 200 of FIG. 2B comprises a flexible membrane 202, an optic 204 and a circumferential peripheral edge 206 coupling the flexible membrane 202 and the optic 204. A membrane coupler 212 is disposed from the internal side of the circumferential peripheral edge 206 to couple the membrane 202 with the peripheral edge 206. An optic coupler 214 is disposed from the internal side of the circumferential peripheral edge 206 to couple the optic 204 to the peripheral edge 206. In contrast to the IOL 100 depicted in FIG. 2A, the optic coupler 214 is not configured to vault the optic 204 toward or away from the flexible membrane 202. Rather, the optic coupler 214, being configured with a series of accordion-like undulations, permit the optic 204 to moveably float in opposing directions along an optical axis A-A in response to the changes of curvature of the flexible membrane 202 caused by the radially compressive forces acting upon the force transmitting area 208.

As with the IOL 100 of FIG. 2A, the circumferential peripheral edge 206 comprises a force transmitting area 208 that is disposed on the external side of the peripheral edge 206 along a portion that opposes the membrane coupler 212. Preferably, the force transmitting area 208 does not extend to the portion of the external side that opposes the optic coupler 214. The portion of the external side that opposes the optic coupler 214 is the stepped-in portion 210. The closed volume 203 maintains a gap or a spaced relation between the flexible membrane 203 and the optic 204 and performs substantially the same functions as described with respect to the closed volume 103 of FIG. 2A.

The change in curvature of the flexible membrane 202 provides the accommodative power change, with radially compressive force. As the flexible membrane 202 changes in curvature, the optic 204 axially displaces toward the flexible membrane 202. This permits the flexible membrane 202 to change shape in an optically uniform manner with a constant volume of fluid, thereby avoiding the problems of non-uniform buckling of the flexible membrane. The dotted lines in FIG. 2B depict the change in curvature of the flexible membrane 202 and the axial displacement of the optic 204 in the presence of an radially compressive force upon the force transmitting area 208 to produce the desired diopter change. As FIG. 2B shows the deformation of the membrane at the dotted line is smooth and would have good optical quality. High period buckling is eliminated which avoids creating a wavy or rippled surface that would have poor optical quality.

FIG. 2C depicts an IOL 300 comprising a flexible membrane 302, an optic 304 and a circumferential peripheral edge 306 coupling the flexible membrane 302 and the optic 304. The membrane coupler 312 couples the flexible membrane 302 to the peripheral edge 306 and the optic coupler 314 couples the optic 304 to the peripheral edge 306.

The peripheral edge 306 comprises a force transmitting area 308 and a stepped-in area 310. Unlike the configuration of the peripheral edges shown in FIGS. 2A and 2B, force transmitting area 308 is located on the external side of the peripheral edge 306 along a portion that opposes the optic coupler 314. Preferably, the force transmitting area 308 does not extend to the portion of the external side that opposes the membrane coupler 312. This configuration permits the force transmitting area 308 to concentrate the transmission of the radially compressive forces applied thereon to the optic 304 via the optic coupler 314 to cause axial displacement of the optic 314 along a central axis A-A. The optic coupler 314 is preferably angled toward the flexible membrane 302 such that it axially-displaces the optic 304 toward the flexible membrane 302 when a radially compressive force is applied onto the force transmitting area 308.

In contrast to the embodiments depicted in FIGS. 2A and 2B, the flexible membrane 302 changes in curvature indirectly as a result of the radially compressive forces. It is the axial displacement of the optic 304 that pushes the fluid contained in the closed volume 304 and exerts a force on the inner surface of the flexible membrane 302 facing the optic 304. Thus, the fluid force exerted on the flexible membrane 302, resulting from the axial displacement of the optic 304, is what directly causes the change in curvature of the flexible membrane 302.

In one preferred embodiment, the IOL 300 further comprises a circumferential channel 305 that is in fluid communication with and included with the volume defining the closed volume 303. The circumferential channel 305 is provided between the internal side of the circumferential peripheral edge 306 and the flexible membrane 302 and functions to further isolate the flexible membrane 302 from the direct radially compressive forces exerted on the peripheral edge 306 and/or the force transmitting area 308 such that the changes in curvature of the flexible membrane 302 results substantially, if not entirely, as a direct result of the fluid pressure from the axial displacement of the optic 304.

The change in curvature of the flexible membrane 302 provides the accommodative power change, with radially compressive force. As the optic 304 axially displaces towards the flexible membrane 302, the flexible membrane 302 changes in curvature. This permits the flexible membrane 302 to change shape in an optically uniform manner with a constant volume of fluid, thereby avoiding the problems of non-uniform buckling of the flexible membrane. The dotted lines in FIG. 2C depict the change in curvature of the flexible membrane 302 and the axial displacement of the optic 304 in the presence of an radially compressive force upon the force transmitting area 308 to produce the desired diopter change. As FIG. 2C shows the deformation of the membrane at the dotted line is smooth and would have good optical quality. High period buckling is eliminated which avoids creating a wavy or rippled surface that would have poor optical quality.

The fluid contained within the closed volumes 103, 203, and 303 of FIGS. 2A-C may be any fluid, preferably selected from the group consisting of silicone oil, fluorinated silicone oil and a polyphenyl ether. In accordance with one embodiment, fluid (213, 313, 413, 513) may be a polyphenyl ether ("PPE"), as described in U.S. Pat. No. 7,256,943, entitled "Variable Focus Liquid-Filled Lens Using Polyphenyl Ethers" to Teledyne Licensing, LLC, the entire contents of which are incorporated herein by reference as if set forth fully herein.

In accordance with another embodiment, the fluid may be a fluorinated polyphenyl ether ("FPPE"). FPPE has the unique advantage of providing tunability of the refractive index while being a chemically inert, biocompatible fluid with dispersion properties. The tunability is provided by the increasing or decreasing the phenyl and fluoro content of the polymer. Increasing the phenyl content will effectively increase the refractive index of the FPPE, whereas increasing the fluoro content will decrease the refractive index of the FPPE while decreasing the permeability of the FPPE fluid through the walls of the IOL.

In another preferred embodiment, closed volume may be filled with a gel. The gel preferably has a refractive index of at least 1.46, 1.47, 1.48, or 1.49. The gel may also preferably have a Young's modulus of 20 psi or less, 10 psi or less, 4 psi or less, 1 psi or less, 0.5 psi or less, 0.25 psi or less and 0.01 psi or less. In a preferred embodiment, the gel is a crosslinked polymer, preferably a crosslinked silicone polymer, and more preferably a crosslinked phenyl siloxane polymer, such as a vinyl-terminated phenyl siloxane polymer or a vinyl-terminated diphenyl siloxane polymer. Other optically clear polymer liquids or gels, in addition to siloxane polymers, may be used to fill the enclosed cavity and such polymers may be branched, unbranched, crosslinked or uncrosslinked or any combination of the foregoing.

A gel has the advantages of being extended in molecular weight from being crosslinked, more self-adherent and also adherent to the walls or opposing sides of the IOL than most liquids. This makes a gel less likely to leak through the walls of the IOL. In order to obtain the combination of accommodative power with relatively small deformations in the curvature of the power changing lens, the gel is selected so as to have a high refractive index while being made of an optically clear material that is characterized as having a low Young's modulus. Thus, in a preferred embodiment, the gel has a refractive index of 1.46 or greater, preferably 1.47 or greater, 1.48 or greater and most preferably 1.49 or greater. At the same time, the gel preferably has a Young's modulus of 10 psi or less, preferably 5 psi or less, and more preferably 1 psi or less. In a particularly preferred embodiment, the gel has a Young's modulus of 0.5 psi or less, preferably 0.25 psi or less, and most preferably 0.01 psi or less. It is understood that at lower Young's modulus, the gel will present less resistance to deformation and thus the greater the deformation of the power changing lens 110 for a given unit of applied force.

The IOLs described in FIGS. 1 and 2A-2C may be implanted directly into a lens capsule or sulcus of a patient's eye with either the flexible membrane or optic being positioned posteriorly. Additionally, the IOLs may be provided as part of a two-piece accommodating intraocular lens assembly as shown in FIGS. 4A-4C comprising a base lens assembly 400 and an IOL.

Figure 3A:
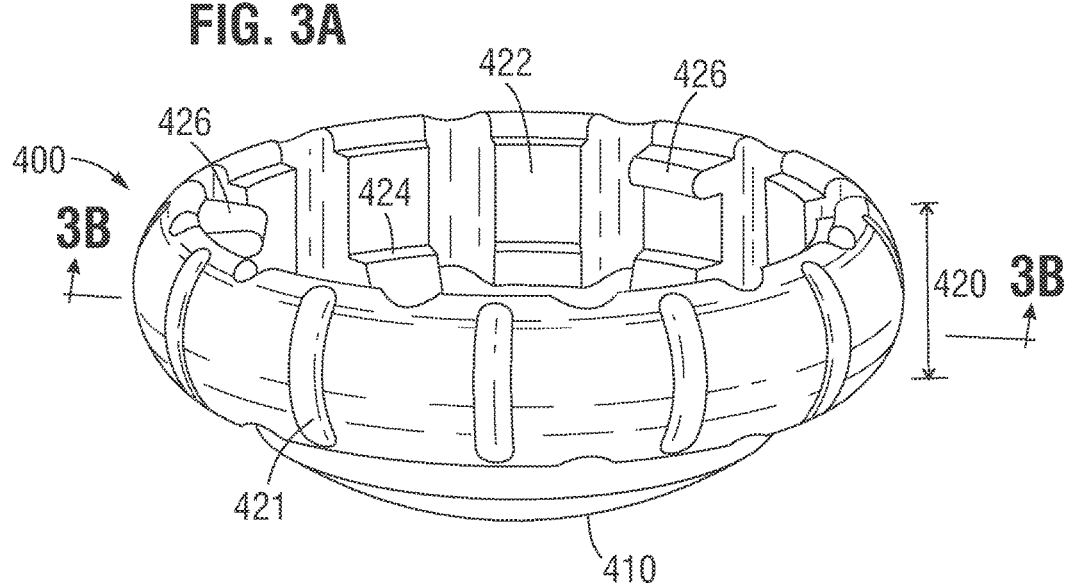
FIG. 3A is a perspective view of a base lens assembly.
Figure 3B:
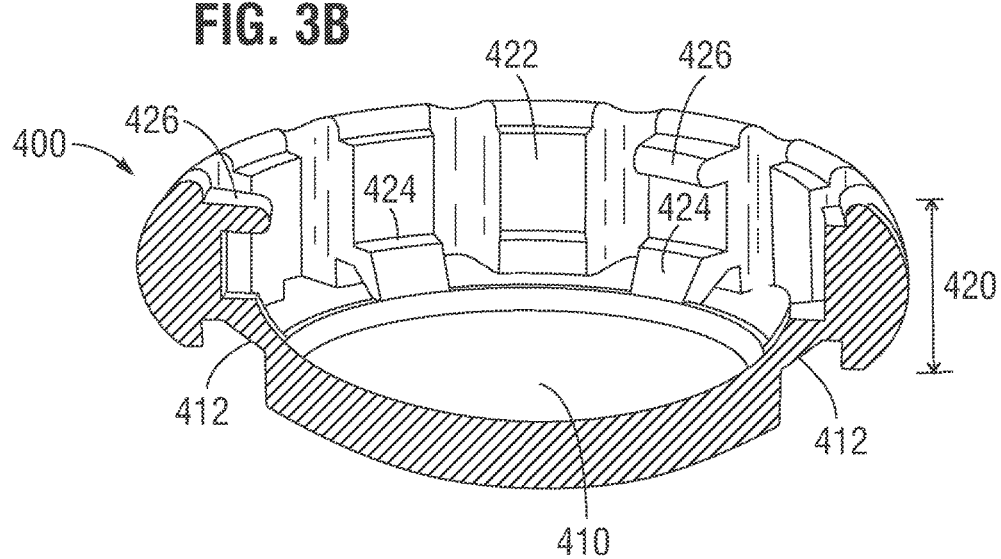
FIG. 3B is a cross-sectional view of the base assembly taken along 3B-3B of FIG. 3A.

FIGS. 3A-3B depict an embodiment of a base lens assembly 400 comprising a base power optic 410 and a haptic system disclosed circumferentially around the base power optic 410. The haptic system comprises an internal surface 422 and an external surface 420 dimensioned and shaped to contact a lens capsule or sulcus of an eye when implanted. The internal surface 422 sized and dimensioned to accommodate an IOL such that the internal surface 422 is in engaging contact with the force transmitting area of the IOL. The haptic system further comprises a plurality of arms 412 having a surface 424 to engage a surface of the IOL that comprises one of the optic or the flexible membrane. The haptic system also comprises a plurality of flanges 426 extending radially inwardly from the internal surface 422 to engage a surface of the IOL that comprises the other one of the surface comprising the optic or flexible membrane. The engaging surface 412 and flanges 426 cooperate to securely maintain the IOL within the base lens assembly 400 and prevent the IOL from becoming dislodged from the base lens assembly 400. A plurality of spaced notices 421 around the external surface of the haptic system may further be provided to permit radial compression of the haptic system.

FIGS. 4A-4C depict a fully-assembled two-piece accommodating intraocular lens assembly comprising an IOL (100, 200, 300) and a base lens assembly 400 assembled together. As can be seen, the force transmitting areas of the respective IOLs are in close engaging contact with the internal surface 422 of the haptic system. In addition, the flanges 426 and the engaging surface 424 are depicted as being in close engaging contact with the side of the IOL that comprises the flexible membrane and the side of the IOL that comprises the optic, respectively. While one orientation of the IOL within the base lens assembly 400 is shown, it is understood that the IOL may be flipped and provided within the base lens assembly 400 in the opposite orientation, with the optic being on top and the flexible membrane facing the base lens 410 of the base lens assembly 400. In a preferred embodiment, a gap is provided between the internal surface 422 of the haptic system 420 and the stepped-in portions (110, 210, 310).

Implantation of the two-piece accommodating intraocular lens assembly may be performed in two steps, with implantation of the base assembly 400 being performed first and implantation and assembly of the IOL within the base assembly 400 being subsequently performed. The advantage to this two-step process is the reduction in the incision size required to implant a lens that has a substantially greater range of accommodation. Moreover, the two-step process also provides flexibility with respect to providing one of two orientations of the IOL, the first of which positions the flexible membrane anteriorly of the eye and the second of which positions the flexible membrane posteriorly of the eye. The clinician may determine and choose the appropriate orientation based on the visual needs of a patient. Additionally the base assembly after implantation may be used to determine the size and power of the IOL that will be implanted.

Example 1

An IOL similar to the IOL shown in FIG. 2A, except the membrane was 200 microns in the center and 100 microns in the periphery, was modeled with a 7 mm overall diameter and a 1.2 mm center thickness. The modeling included a fluid with a refractive index of 1.49 inside of the closed volume of the IOL. Various modulus materials were modeled and evaluated by finite element analysis. The results demonstrated a power change of 5 D with a 3 mm aperture. The initial diopter power was 22.0 D and the final diopter was 27.2 D.

Example 2

The IOL in Example 1 was built using an optic quality silicone material for the membrane and the closed volume was filled with a silicone fluid having a refractive index of 1.49. Testing was performed with an artificial capsule under similar load configuration in Example 1. The diopter power change measured using a 3 mm aperture was 5.5 D. The power changed from 23 D to 28.5 D with acceptable optical quality throughout the range of power change.

Example 3

The IOL tested in Example 2 was then placed inside of a base lens assembly that was placed inside of an artificial lens capsule. The base lens assembly was similar in design to the lens shown in FIG. 3A. Testing was performed under similar load conditions as Example 2. The base power lens had a −8.5 D power and the power changing lens had a power of 23 D. When the IOL and the base lens assembly were assembled together, the combined power was measured at 14.5 D with a 3 mm aperture. The diopter power change measured using a 3 mm aperture was 5.5 D. The diopter power changed from 14.5 D to 21.0 D with acceptable optical quality throughout the range of power change.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

The invention claimed is:

1. A two-piece accommodating intraocular lens assembly comprising:
an accommodating intraocular lens (IOL) comprising:
  an optic;
  a flexible membrane;
  a peripheral edge coupled to the optic and the flexible membrane, the peripheral edge being an outer periphery of the accommodating IOL and comprising an external circumferential surface having a force transmitting area having an annular shape along the external circumferential surface; and
  a closed volume spacing apart the optic and the flexible membrane and configured to contain a fluid; and
a base lens assembly comprising a base power optic and a haptic system circumferentially around the base power optic, the haptic system having a radially-compressible outer circumference configured to engage a capsular bag of a patient's eye, and an internal surface in engaging contact with the force transmitting area of the accommodating IOL,
wherein the radially-compressible outer circumference completely surrounds the accommodating IOL and is uniformly compressible when engaged with the capsular bag;
wherein the optic of the accommodating IOL is disposed between the flexible membrane and the base power optic along a central axis,
wherein the engaging contact enables external forces exerted on the outer circumference of the haptic system to be radially transmitted to the force transmitting area of the accommodating IOL, causing the force transmitting area to be radially compressed resulting in a change in curvature of the flexible membrane, without contact between the flexible membrane and the optic, and
wherein, by virtue of pressure of the closed volume, the change in curvature of the flexible membrane causes an axial displacement of the optic further away from the base power optic.

2. The two-piece accommodating intraocular lens assembly of claim 1, wherein only the force transmitting area of the external circumferential surface is in contact with the internal surface of the haptic system.

3. The two-piece accommodating intraocular lens assembly of claim 1, wherein the base lens assembly further comprises supporting flanges extending radially inwardly from the internal surface to contact an anterior side of the accommodating IOL that comprises the flexible membrane.

4. The two-piece accommodating intraocular lens assembly of claim 1, further comprising a plurality of spaced notches disposed around an external surface of the haptic system.

5. The two-piece accommodating intraocular lens assembly of claim 1, wherein the base lens assembly further comprises a plurality of undulations in the circumferential direction between the outer circumference of the haptic system and the peripheral edge of the accommodating IOL.

6. The two-piece accommodating intraocular lens assembly of claim 1, wherein the inner surface of the haptic system comprises a plurality of spaced-apart surfaces, and wherein the force transmitting area of the accommodating IOL is in engaging contact with the inner surface at the plurality of spaced apart surfaces and is not in contact with the inner surface between the plurality of spaced-apart surfaces.

7. The two-piece accommodating intraocular lens assembly of claim 1, wherein the base lens assembly further comprises at least three spaced apart arms, each arm having an outer end adjacent to the internal surface and an inner end coupled with a periphery of the base power optic at spaced part locations, the inner ends of the arms being spaced apart from each other.

8. The two-piece accommodating intraocular lens assembly of claim 1, wherein the base lens assembly further comprises a plurality of spaced apart notches disposed along the outer circumference.

* * * * *